United States Patent [19]

Miner et al.

[11] Patent Number: 5,827,542
[45] Date of Patent: Oct. 27, 1998

[54] QUICK ACTING CHEMICAL STERILANT

[75] Inventors: Norman A. Miner; William H. Woller; Edward L. Anderson; David W Hobson, all of San Antonio, Tex.

[73] Assignee: Healthpoint, Ltd., San Antonio, Tex.

[21] Appl. No.: 600,058

[22] Filed: Feb. 12, 1996

[51] Int. Cl.⁶ .......................... A01N 37/00; A01N 37/16; A01N 59/00; A61L 2/18
[52] U.S. Cl. .......................... 424/616; 424/613; 424/614; 424/615; 514/574; 514/714; 422/12; 422/28; 422/29
[58] Field of Search ...................... 424/613–616; 514/557, 558, 560, 574; 422/12, 28, 29

[56] References Cited

U.S. PATENT DOCUMENTS

| | | | |
|---|---|---|---|
| 3,684,477 | 8/1972 | Blumbergs et al. | 71/67 |
| 4,051,058 | 9/1977 | Böwing et al. | 252/186 |
| 4,051,059 | 9/1977 | Bowing et al. | 252/186 |
| 4,259,383 | 3/1981 | Eggensperger et al. | 428/72 |
| 4,477,438 | 10/1984 | Willcockson et al. | 424/130 |
| 4,715,980 | 12/1987 | Lopes et al. | 252/106 |
| 4,743,447 | 5/1988 | Le Rouzic et al. | 424/130 |
| 4,986,963 | 1/1991 | Corcoran et al. | 422/30 |
| 5,008,079 | 4/1991 | Wutzler et al. | 422/28 |
| 5,055,287 | 10/1991 | Kessler | 424/613 |
| 5,084,239 | 1/1992 | Moulton et al. | 422/22 |
| 5,122,340 | 6/1992 | Shimamura et al. | 422/28 |
| 5,200,189 | 4/1993 | Oakes et al. | 424/405 |
| 5,244,629 | 9/1993 | Caputo et al. | 422/22 |
| 5,262,126 | 11/1993 | Shimamura et al. | 422/28 |
| 5,266,587 | 11/1993 | Sankey et al. | 514/417 |
| 5,269,959 | 12/1993 | Schreibman | 252/100 |
| 5,279,735 | 1/1994 | Cosentino et al. | 210/321.69 |
| 5,286,448 | 2/1994 | Childers | 422/28 |
| 5,310,524 | 5/1994 | Campbell et al. | 422/33 |
| 5,335,373 | 8/1994 | Dangman et al. | 2/161.7 |
| 5,344,652 | 9/1994 | Hall, II et al. | 424/405 |
| 5,357,636 | 10/1994 | Dresdner, Jr. et al. | 2/161.7 |
| 5,384,091 | 1/1995 | Rontome et al. | 422/30 |
| 5,389,336 | 2/1995 | Childers | 422/28 |
| 5,395,530 | 3/1995 | Robertson et al. | 210/632 |
| 5,400,818 | 3/1995 | Cosentino et al. | 137/551 |
| 5,409,713 | 4/1995 | Lokkesmoe et al. | 424/616 |
| 5,413,758 | 5/1995 | Caputo et al. | 422/22 |
| 5,674,538 | 10/1997 | Lokkesmoe et al. | 424/616 |

FOREIGN PATENT DOCUMENTS

| | | |
|---|---|---|
| 2 584 503 | 1/1987 | France . |
| 59-196385 | 11/1984 | Japan . |
| 1 570 492 | 7/1980 | United Kingdom . |

OTHER PUBLICATIONS

Chemical Abstracts 94:151097d, 1981.
Chemical Abstracts 102:135948K, 1985.
WPIDS Abstract 96–196557, 1996.
WPIDS Abstract 94–118027, 1994.
Chemical Abstracts 96:135353, 1982.
Chemical Abstracts 91:134709, 1979.
WPIDS Abstract 82–38444E, 1982.
The Merck Index, 10th Edition, Merck & Co., Inc., Rahway, NJ, pp. 1288–1299, Item #8854, 1983.
Miner, Apr. 1992, vol. 10, No. 3 Copyright 1992, Mayworm Associates, Inc.
Portner et al., Copyright 1968 by the American Society for Microbiology Reprinted from Appl. Microbiol. 16, 1782–1785 (1968).
Gröschel, Chemical Germicides in Health Care by William A. Rutala, Published by Association for Professionals in Infection Control and Epidemiology and Polyscience Publications Inc., 1995, pp. 73–81.

*Primary Examiner*—John Pak
*Attorney, Agent, or Firm*—Zarley, McKee, Thomte, Voorhees & Sease

[57] ABSTRACT

A low odor, aqueous, quick acting room temperature disinfectant solution primarily useful for medical instruments to disinfect within a half hour or less. The composition comprises a reacting or synergistic combination of hydrogen peroxide and from about 1% to 30% by weight of a water soluble organic acid or salt form thereof with the acid preferably being selected from the group consisting of malonic and succinic acids.

16 Claims, No Drawings

QUICK ACTING CHEMICAL STERILANT

BACKGROUND OF THE INVENTION

Medical, dental and other instruments are often made of high quality stainless steel that can be cleaned and sterilized between uses for different patients by high temperature steam under pressure. This sterilization procedure is quick, reliable, odorless, non-toxic and inexpensive. In contrast to this situation, more and more instruments are now made of heat-sensitive plastic, rubber, glass lenses and electronic components. These flexible, flexible-lensed, and rigid-lensed instruments allow relatively non-invasive diagnostic and treatment procedures within the body. The non-invasive procedures allowed by these heat-sensitive instruments are responsible for great advances in medical practice. During use, these instruments can be contaminated with deadly pathogens such as the Human Immunodeficiency Virus (HIV), hepatitis viruses, and antibiotic drug-resistant tuberculosis and other bacteria. For these reasons, it is imperative that these heat-sensitive instruments be sterilized of all microbes prior to each use. The chemical germicides available for sterilization of heat-sensitive instruments have in the past had many problems that made their use difficult.

The antimicrobial properties of hydrogen peroxide have been known for many years. However, 6% hydrogen peroxide requires a minimum of 6 hours at room temperature to pass the standard Association of Official Analytical Chemists (AOAC) Sporicidal Test. This is the test that defines "sterilant" for liquid chemical germicides in the United States. The antimicrobial properties of peracetic acid are also well known. Peracetic acid has a very sharp pungent odor, and is known as a tumor-promoting agent when tested on mouse skin. For these reasons, the use of peracetic acid as a chemical sterilant is limited to low concentrations used with enclosed systems.

Antimicrobial synergism between hydrogen peroxide and peracetic acid is a well established fact. Such compositions are prepared by mixing hydrogen peroxide and acetic acid to give equilibrated solutions of hydrogen peroxide, acetic acid, and peracetic acid. There is a great deal of scientific and patent literature regarding hydrogen peroxide-peracetic acid solutions for sterilization. By way of example only, Minntech Corporation of Minneapolis, Minn., has a kit or sterilization console for disinfecting with hydrogen peroxide-peracetic acid solutions (U.S. Pat. No. 5,400,818). However, this combination is limited by the same problems of pungent odor and potential toxicity as peracetic acid alone. This often means that such formulations are used at such dilute concentrations that rapid sporicidal activity is lost, or the solutions are limited to enclosed systems that contain the pungent fumes.

Steris Corporation of Mentor, Ohio, markets a Steris System 1 product. This uses a low concentration of peracetic acid (about 0.2%) contained within a machine, and is heated to 122° F. to achieve rapid sterilization. The relatively low peracetic acid concentration, coupled with the high temperature, breaks down the peracetic acid, limiting it to one single use cycle. The heated, enclosed, single-use machine system is expensive and less than desirable.

Another chemical sterilant is 2% alkaline glutaraldehyde. Glutaraldehyde requires about 10 hours at 25° C. to pass the AOAC Sporicidal Test. Because of this long exposure time, the use of glutaraldehyde is usually compromised to accept disinfection from a shorter exposure time rather than the safer condition of sterilization. Furthermore, glutaraldehyde has an odor that irritates eye, nose, and throat mucous membranes. Repeated exposure to glutaraldehyde causes headaches and allergic reactions for some people. For these reasons, glutaraldehyde is a less than desirable chemical germicide.

Many chemicals that contain chlorine are rapidly sporicidal and capable of sterilization. Examples are bleach, the active agent of which is $HOCl$, $HClO_2$, $ClO_2$, and $HCl$. However, while these chemicals are rapidly sporicidal, they are too corrosive to metals and elastomers to find any practical use in sterilization of medical, dental and other instruments.

It can therefore be seen that there is a continuing need for an effective, practical, safe, affordable sterilant for heat-sensitive instruments, as well as for all applications that are beyond the scope of steam sterilization. This invention has as its primary objective the fulfillment of this need.

SUMMARY OF THE INVENTION

This invention relates to a rapid acting room temperature sterilant. It is a low odor, aqueous disinfecting solution having a pH within the range of 2–6. It comprises in combination a solution of from about 1% to about 30% by weight of peroxide capable of releasing hydroxyl free radicals, and from about 1% to about 30% by weight of a water soluble organic acid or salt form of a $C_3$ or higher mono, or a di-, tri-, or poly carboxylic organic acid, with the organic acid preferably selected from the group consisting of malonic acid and succinic acid, or combinations thereof. It is believed there may be a reaction between the peroxide and carboxylic acids that produce a third chemical or condition that causes rapid kill of bacterial spores and other microbes at ambient temperatures (18° C.–24° C.) in short times (i.e. within 30 minutes). The carboxylic acids that can be used with peroxides can be selected from a large group to be relatively odor-free, non-toxic, soluble and inexpensive.

DETAILED DESCRIPTION OF THE INVENTION

The sterilizing and disinfecting solutions of this invention have a variety of uses. The solutions have excellent sterilization and disinfecting properties and can be used to sterilize sophisticated medical instruments such as endoscopes without causing damage to sensitive parts of such instruments.

The fact that this process can be used with endoscopic instruments is significant since relatively non-invasive endoscopic procedures have revolutionized the way that surgery is performed. As earlier mentioned, few rigid or flexible endoscopes can be sterilized by the quick and sure method of steam sterilization because the plastic, rubber and precisely-positioned glass lenses of endoscopes make them incompatible with the heat of a steam sterilizer. Instead they must be sterilized using lower temperatures and typically slower processes. They also must use a sterilizing solution that is non-corrosive.

Endoscopes are but one example of the type of instrument that can be effectively sterilized with the present compositions. Conventional surgical instruments of all types, micro-surgery instrument sets, anesthesia equipment, etc. can also be treated. Generally, the composition disclosed herein can be used for sterilization of any products that enter sterile tissue or the vascular system or have tissue contact during any surgeries. Necessarily, if the solution is effective for these critical medical instruments, it also can be used for intermediate level and low level instruments and surfaces. Because the formulation is relatively odorless and non-toxic, one can sterilize surfaces that formerly were only disinfected or sanitized, or one can dilute the formula for disinfection rather than sterilization. The composition may also be used as an antiseptic to kill germs on skin. It is therefore versatile in use.

It had previously been thought that effectiveness of hydrogen peroxide and peracetic acid combinations to pass standard "AOAC" sterilization tests was due to the substantial enhancement of formation of free hydroxy radicals from the "per" acid in combination with hydrogen peroxide. Accordingly, it was thought necessary to add peroxyacetic acid directly to germicidal formulations. Quite surprisingly, the inventors found that it was not necessary to add the toxic and malodorous peracetic acid to sterilizing formulations. Instead, certain lower carboxylic acids selected for their solubility, lack of odor, and non-toxic nature can be used in combination with hydrogen peroxide to achieve sterility at ambient temperatures and short exposure times. In particular, the carboxylic acid could be a $C_3$ or higher mono or a di- or poly carboxylic acid of up to $C_{12}$ chain length and can be saturated or unsaturated. As a result of this composition, complex and expensive equipment needed to contain toxic chemicals can be eliminated, and since the acids employed are weak organic acids, corrosion of materials is significantly reduced. As a result, providing the levels herein described are used, there is a reacting or synergistic relationship between the defined water soluble organic acid and the peroxide such that even at lower temperatures non-corrosive sterilization is achieved. Moreover, the chemicals are generally inexpensive and odor-free, and are therefore economically and simply packaged. Of course, less odor and less toxic mean that higher concentration can be used with accompanying faster rate of sterilization. At higher exposure temperatures of 30°, 40°, or 50° C., for example, the exposure time needed to achieve sterilization is even faster than at ambient temperatures.

The first component of the composition is from about 1% to about 30% by weight of a peroxide. Preferably, the amount of peroxide is from about 1% by weight to about 12% by weight of the disinfecting solution, and most preferably from about 6% by weight to about 10% by weight of the disinfecting solution. The preferable concentration of peroxide may be varied depending on the application from lower concentration for an antiseptic to higher concentrations for a low-temperature, rapid-acting sterilant. The peroxide of choice is, of course, the most commonly available peroxide, hydrogen peroxide. However, the invention is not limited to hydrogen peroxide, and other peroxy compounds may be employed. These include, for example, perborates, saturated and unsaturated peralkanoic acids such as peracetic acid, performic acid, perpropionic acid, etc. The critical factor is that it be a water soluble peroxide compound that is compatible with the weak carboxylic acid component.

The weak carboxylic acid component of the present invention is preferably a di- acid of lower $C_{12}$ or less carbon length carboxylic acid preferably selected from the group consisting of malonic acid and succinic acid. Also, examples of acids in this class would be malic, oxalic and tartaric acids. These acids, when in the proper concentrations, are low odor, reasonably soluble and non-corrosive. The amount of the carboxylic acid component generally would be within the range of from about 1.0% by weight to 30% by weight of sterilizing or disinfecting solution, preferably from about 1% by weight to about 12% by weight of the solution, and most preferably from about 3% by weight to about 6% by weight of the solution composition. As with the peroxide, the preferred concentration of carboxylic acids is related to the intended end use.

Generally speaking, and as a guideline, the peroxide component should have a concentration of within the range of 0.2M to about 10M, preferably within the range of 0.2M to 4.0M. The organic acid component should have a concentration within the range of 0.05M to 4.0M, and preferably of 0.05M to 2.0M.

While acetic acid is unacceptable by itself because of its normal pungent odor, it is possible that some acetic acid, in combination with other of the acids described here, can be successfully used. Thus the key to the present invention is the presence of the herein-described combination or perhaps the reaction product thereof.

Generally, the amount of peroxide component and the amount of carboxylic acid component are balanced such that the pH will be within the range of about 2.0 to 6.0, preferably about 3.0 to 5.0.

While a suitable sterilizing and disinfecting solution can be achieved with these two components only, as is understood by those skilled in the art, other ingredients may be added. In fact, the sterilizing and disinfecting capabilities can be enhanced by adding a small amount of detergent such as nonionic or anionic detergent. The amount of detergent can be within the range of from about 0.05% by weight to about 1.0% by weight, preferably from about 0.1% by weight to about 0.5% by weight. The amount of detergent should be enough to enhance the sterilization and disinfection, but less than the amount which would provide substantial sudsing.

Suitable synthetic detergents are well known to those of ordinary skill in the art, but generally these surface active agents can be selected from the group consisting of anionic and nonionic surfactants. Non-ionic, ether-linked surfactants such as Laureth®4 or Laureth®23 are preferred.

Alkyl sulfate surfactants are a type of anionic surfactant of importance for use herein. Alkyl sulfates have the general formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), substituted or unsubstituted ammonium cations such as methyl-, dimethyl-, and trimethyl ammonium and quaternary ammonium cations, e.g., tetramethylammonium and dimethyl piperdinium, and cations derived from alkanolamines such as ethanolamine, diethanolamine, triethanolamine, and mixtures thereof, and the like. Typically, alkyl chains of $C_{12-16}$ are preferred for lower wash temperatures (e.g., below about 50° C.) and $C_{16-18}$ alkyl chains are preferred for higher wash temperatures (e.g., above about 50° C.).

Alkyl alkoxylated sulfate surfactants are another category of useful anionic surfactant. These surfactants are water soluble salts or acids typically of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperydinium and cations derived from alkanolamines, e.g., monoethanolamine, diethanolamine, and triethanolamine, and mixtures thereof. Exemplary surfactants are $C_{12}-C_{18}$ alkyl polyethoxylate (1.0) sulfate, $C_{12}-C_{18}$ alkyl polyethoxylate (2.25) sulfate, $C_{12}-C_{18}$ alkyl polyethoxylate (3.0) sulfate, and $C_{12}-C_{18}$ alkyl polyethoxylate (4.0) sulfate wherein M is conveniently selected from sodium and potassium.

Other anionic surfactants useful for detersive purposes can also be included in the compositions hereof. These can include salts (including, for example, sodium, potassium, ammonium, and substituted ammonium salts such as mono-, di- and triethanolamine salts) of soap, $C_9-C_{20}$ linear alkylbenzenesulphonates, $C_8-C_{22}$ primary or secondary alkanesulphonates, $C_8-C_{24}$ olefinsulphonates, sulphonated polycarboxylic acids, alkyl glycerol sulfonates, fatty acyl glycerol sulfonates, fatty oleyl glycerol sulfates, alkyl phenol ethylene oxide ether sulfates, paraffin sulfonates, alkyl phosphates, isothionates such as the acyl isothionates, N-acyl taurates, fatty acid amides of methyl tauride, alkyl succinamates and sulfosuccinates, monoesters of sulfosuccinate (especially saturated and unsaturated $C_{12}-C_{18}$ monoesters) diesters of sulfosuccinate (especially saturated and unsaturated $C_6-C_{14}$ diesters), N-acyl sarcosinates, sulfates of alkylpolysaccharides such as the sulfates of alkylpolyglucoside, branched primary alkyl sulfates, alkyl polyethoxy carboxylates such as those of the formula $RO(CH_2CH_2O)_kCH_2COO-M+$ wherein R is a $C_8-C_{22}$ alkyl, k is an integer from 0 to 10, and M is a soluble salt-forming cation, and fatty acids esterified with isethionic acid and neutralized with sodium hydroxide. Further examples are given in *Surface Active Agents and Detergents* (Vol. I and II by Schwartz, Perry and Berch).

Suitable nonionic detergent surfactants are generally disclosed in U.S. Pat. No. 3,929,678, Laughlin et al., issued Dec. 30, 1975, at column 13, line 14 through column 16, line 6, incorporated herein by reference. Exemplary, non-limiting classes of useful nonionic surfactants are listed below.

The polyethylene, polypropylene, and polybutylene oxide condensates of alkyl phenols. In general, the polyethylene oxide condensates are preferred. These compounds include the condensation products of alkyl phenols having an alkyl group containing from about 6 to about 12 carbon atoms in either a straight chain or branched chain configuration with the alkaline oxide. These compounds are commonly referred to as alkyl phenol alkoxylates, (e.g., alkyl phenol ethoxylates).

The condensation products of aliphatic alcohols with from about 1 to about 25 moles of ethylene oxide. The alkyl chain of the aliphatic alcohol can either be straight or branches, primary or secondary, and generally contains from about 8 to about 22 carbon atoms. Particularly preferred are the condensation products of alcohols having an alkyl group containing from about 10 to about 20 carbon atoms with from about 2 to about 18 moles of ethylene oxide per mole of alcohol.

The condensation products of ethylene oxide with a hydrophobic base formed by the condensation of propylene oxide with propylene glycol. Examples of compounds of this type include certain of the commercially-available Pluronic TM surfactants, marketed by BASF.

The condensation products of ethylene oxide with the product resulting from the reaction of propylene oxide and ethylenedianine. Examples of this type of nonionic surfactant include certain of the commercially available Tetronic TM compounds, marketed by BASF.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms 31 and a moiety selected from the group consisting of alkyl and hydroxyalkyl moieties of from about 1 to about 3 carbon atoms.

Semi-polar nonionic detergent surfactants include the amine oxide surfactants having the formula

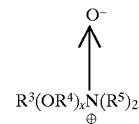

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}-C_{18}$ alkyl dimethyl amine oxides and $C_8-C_{12}$ alkoxy ethyl dihydroxy ethyl amine oxides.

Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions, thus giving a glucose or galactose as opposed to a glucoside or galactoside). The intersaccharide bonds can be, e.g., between the one position of the additional saccharide units and the 2-, 3-, 4-, and/or 6- positions on the preceding saccharide units.

Fatty acid amide surfactants having the formula:

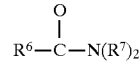

wherein $R^6$ is an alkyl group containing from about 7 to about 21 (preferably from about 9 to about 17) carbon atoms and each $R^7$ is selected from the group consisting of hydrogen, $C_1-C_4$ alkyl, $C_1-C_4$ hydroxyalkyl, and $-(C_2H_4O)_xH$ where x varies from about 1 to about 3.

In addition to the above, if desired, corrosion inhibitors at very minor levels can be used, i.e. at levels of 0.01% to 0.1% on a weight basis. Suitable corrosion inhibitors can include those available and known, for example, complex fatty amine salts such as n,n'dibutylthiourea, etc.

Nonionic ether linked surfactants are preferred such as Laureth®23 or Laureth®4.

In addition to all of the above, as is well understood by those skilled in the art, other minors can be employed to make the basic composition more pharmaceutically elegant. For example, odorants can be added at very minor levels as can dyes, diluents such as alcohol, buffers, etc. With the exception of diluents such as alcohols which are used at higher levels, the levels of these minors are generally not more than 0.001% to 0.01% by weight.

The composition can be used as a sterilant for medical and dental equipment, implanted medical and dental devices and appliances, can be used as a disinfectant for inanimate surfaces, can be used as an antiseptic for skin disinfection, such as for patient preoperative skin disinfection or health personnel, a hand wash, may be used as a disinfectant for contact lenses, an oral disinfectant or antiseptic, and can be used generally for conventional, intermediate and low level disinfection, and as a sterilant in industrial applications.

Packaging of the composition is not complex. It may be prepackaged in dry form if desired with instructions for mixing solutions on the spot, or it may be prepackaged in solution form, ideally in two packages (one the peroxide and one the organic acid component) to be mixed at point of use. This enhances freshness and accuracy of compliance with directions.

The following examples are offered to illustrate, but not limit, the process of the present invention and to demonstrate the surprising result that satisfactory results in comparison with acetic acid can be achieved with weaker longer chain acids such as succinic acid.

Historically, the Environmental Protection Agency regulates germicides in the United States, and the test for a sterilizing claim (a sterilant) by a liquid germicide is the Association of Official Analytical Chemists (AOAC) Sporicidal Activity of Disinfectants Test 966.04. This test exposes spores dried onto carrier surfaces to the germicide. To make a label claim as a sterilant, a germicide must produce 720 sterile cylinders of 720 total cylinders within a specified exposure time and temperature range. A legal definition of sterilant in the United States is one that can pass this test. In the following tests peroxide composition alone was compared with an acetic acid composition alone and with sodium acetate composition with regard to ability to sterilize carriers labeled with spores according to the methods of the AOAC Sporicidal Test.

TABLE I

| Formulation | Number of Positive (+) Cylinders per Total Number Tested. 30 Min. Exposure at 20 ± 1° C. | Percent Sterile Cylinders |
|---|---|---|
| 6% $H_2O_2$, pH 4.7 | 20/20 | Zero |
| 6% $H_2O_2$ + 0.5% Acetic Acid pH 2.7 | 2/20 | 90% |
| 0.5% Acetic Acid pH 2.8 | 20/20 | Zero |
| 6% $H_2O_2$ + 0.5% Sodium Acetate pH 6.7 | 20/20 | Zero |
| 0.5% Sodium Acetate pH 7.7 | 20/20 | Zero |

This test was repeated with some modifications in an attempt to sterilize 100% of the *C. sporogenes*-labeled cylinders. The results were as follows.

TABLE II

| Formulation | Time in Min. at 20 ± 1° C. | Number of Positive Cylinders (+) Per Total Number Tested | Percent Sterile Cylinders |
|---|---|---|---|
| 8% $H_2O_2$ pH 4.5 | 30 | 20/20 | Zero |
| 8% $H_2O_2$ + 2% Acetic Acid pH 2.4 | 10 | 9/20 | 55% |
|  | 20 | 0/20 | 100% |
|  | 30 | 0/20 | 100% |
| 8% $H_2O_2$ + 1% Acetic Acid Ph 2.6 | 10 | 10/20 | 50% |
|  | 20 | 8/20 | 60% |
|  | 30 | 0/20 | 100% |
| 8% $H_2O_2$ + 0.5% Acetic Acid pH 2.7 | 10 | 11/20 | 45% |
|  | 20 | 9/20 | 55% |
|  | 30 | 0/20 | 100% |
| 2% Acetic Acid pH 2.7 | 30 | 20/20 | Zero |

Tests were done at ambient conditions comparing the rapid sporicidal activity of hydrogen peroxide in combination with the carboxylic acids acetic, malonic, succinic, glutaric and citric acids. Compositions from the data are reported in Table III.

TABLE III

Sterilization of *C. sporogenes*-labeled porcelain cylinders by formulations of $H_2O_2$ plus acetic, malonic, or succinic acid.

| Formulation | Exposure Time Min. × 20° C. | Percentage of Twenty *C. sporogenes*-labeled Cylinders Sterilized |
|---|---|---|
| 8% $H_2O_2$ plus 1% acetic acid pH 2.5 | 10 | 50% |
|  | 20 | 80 |
|  | 30 | 100 |
| 8% $H_2O_2$ plus 1% malonic acid pH 1.8 | 10 | Zero % |
|  | 20 | 40 |
|  | 30 | 85 |
| 8% $H_2O_2$ plus 0.5% malonic acid pH 1.9 | 10 | 5% |
|  | 20 | 25 |
|  | 30 | 100 |
| 8% $H_2O_2$ plus 1% succinic acid pH 2.4 | 10 | Zero % |
|  | 20 | 15 |
|  | 30 | 95 |

Further tests combined $H_2O_2$ with glutaric acid and citric acid. The results are shown in Table IV and V.

TABLE IV

Sterilization of *C. sporogenes*-labeled porcelain cylinders by formulations of $H_2O_2$ plus acetic, glutaric, and citric acid.

| Formulation | pH Value | Exposure Time Min × 20° C. | Percentage of Twenty *C. sporogenes*-labeled Cylinders Sterilized |
|---|---|---|---|
| 8% $H_2O_2$ plus 0.2M Acetic Acid | 2.4 | 20 | 100% |
|  |  | 30 | 100 |
|  | 4.3 | 20 | 100% |
|  |  | 30 | 100 |
| 8% $H_2O_2$ plus 0.2M Glutaric Acid | 2.2 | 20 | 100 |
|  |  | 30 | 100 |
|  | 5.0 | 20 | Zero |
|  |  | 30 | Zero |
| 8% $H_2O_2$ plus 0.2M Citric Acid | 1.9 | 20 | Zero |
|  |  | 30 | Zero |
|  | 6.6 | 20 | Zero |
|  |  | 30 | Zero |

TABLE V

Surviving Colonies of Wet Spores of *B. subtilis* After Exposure to Formulations of $H_2O_2$ Plus Acetic Acid, Glutaric Acid, or Citric Acid.

| Formulation | pH Value | Exposure Time Min × 20° | \| Surviving Colonies of *B. subtilis* at Dilution Factors | | | | |
|---|---|---|---|---|---|---|---|
| | | | $5 \times 10^1$ | $5 \times 10^2$ | $5 \times 10^3$ | $5 \times 10^4$ | $5 \times 10^5$ |
| 8% $H_2O_2$ plus 0.2M Acetic Acid | 2.8 | 15 | | 19 | 1 | Zero | Zero |
| | | 30 | Zero | Zero | Zero | | |
| | | 60 | Zero | Zero | Zero | | |
| | 4.4 | 15 | | 236 | 121 | 26 | 1 |
| | | 30 | Zero | Zero | Zero | | |
| | | 60 | Zero | Zero | Zero | | |
| 8% $H_2O_2$ plus 0.2M Glutaric | 2.6 | 15 | CONF | CONF | CONF | 265 | 70 |
| | | 30 | | 25 | 13 | | |
| | | 60 | Zero | Zero | Zero | | |
| | 5.0 | 15 | CONF | CONF | CONF | TNTC | 101 |
| | | 30 | | TNTC | 206 | 39 | |
| | | 60 | Zero | Zero | Zero | | |
| 8% $H_2O_2$ plus 0.2M Citric | 2.0 | 15 | CONF | CONF | CONF | TNTC | 198 |
| | | 30 | CONF | CONF | CONF | TNTC | |
| | | 60 | CONF | CONF | TNTC | | |
| | 6.4 | 15 | CONF | CONF | CONF | CONF | 283 |
| | | 30 | CONF | CONF | CONF | CONF | |
| | | 60 | CONF | CONF | CONF | | |

CONF = Confluent = in excess of 1000 colonies all touching together (confluent).
TNTC = Too Numerous to Count = 300–1000 colonies/plate.

The following example in Table VI compares the rate of kill of *B. subtilis* spores by formulations of $H_2O_2$ plus acetic, malonic, or succinic acid. The test method was wet spores of *B. subtilis* in suspension (not on carriers). This is a quantitative test that allows comparison of formulations with more precision than a qualitative (sterile or not sterile) test such as the AOAC Sporicidal Test. The results are reported below.

TABLE VI

| Formula Number | Formula Description | pH | D-values in Min.* |
|---|---|---|---|
| 1. | 8% $H_2O_2$ + 0.2M (1.2%) acetic acid, | pH 2.7 | 7.5 |
| 2. | 8% $H_2O_2$ + 0.2M (1.2%) acetic acid, | pH 4.2 | 8.5 |
| 3. | 8% $H_2O_2$ + 0.2M (2.1%) malonic acid, | pH 1.8 | 8.5 |
| 4. | 8% $H_2O_2$ + 0.2M (2.1%) malonic acid, | pH 3.0 | 7.8 |
| 5. | 8% $H_2O_2$ + 0.2M (2.4%) succinic acid, | pH 2.4 | 6.0 |
| 6. | 8% $H_2O_2$ + 0.2M (2.4%) succinic acid, | pH 4.2 | 9.0 |

*The D-values were calculated as the time to kill four $\log_{10}$ of *B. subtilis* divided by four.

The general conclusion is that combinations of 8% $H_2O_2$ plus acetic, malonic, or succinic acid surprisingly have about the same rate of kill of *B. subtilis* spores (wet) in suspension. The more acid pH values of about 2–3 were consistently killing faster than the less acid pH values of above 4.

The tests shown in Tables VII and VIII measure the relationship between increasing concentrations of acetic or succinic acid plus 8% $H_2O_2$ and the rate of kill of wet spores of *B. subtilis*. The test using suspensions of wet spores of *B. subtilis*, and measuring surviving spores as a function of exposure time to various formulations is a quantitative test that is better able to measure small differences between formulations than the AOAC Sporicidal Test. All tests were at 20°±1° C.

Acetic Acid:

The formulations tested with acetic acid, and D-value results were as follows:

TABLE VII

| Formula Number | Formula Description | pH Value | D-value |
|---|---|---|---|
| 1. | 8% $H_2O_2$ 1.0M (6%) Acetic Acid 0.5% BioTerge AS-40 | 4.2 | less than 3 Min. |
| 2. | 8% $H_2O_2$ 0.5M (3%) Acetic Acid 0.5% BioTerge AS-40 | 4.2 | 3.5 Min. |
| 3. | 8% $H_2O_2$ 0.25M (1.5%) Acetic Acid 0.5% BioTerge AS-40 | 4.3 | 3.75 Min. |
| 4. | 8% $H_2O_2$ 0.125M (0.75%) Acetic Acid 0.5% BioTerge AS-40 | 4.3 | 4.0 Min. |

BioTerge is a trademark of Stepan Company and is a sodium olefin sulfonate

The formulations tested with succinic acid, and D-value results were as follows in Table VIII:

TABLE VIII

| Formula Number | Formula Description | pH Value | D-value |
|---|---|---|---|
| 1. | 8% $H_2O_2$ 1.0M (11.8%) Succinic Acid 0.5% BioTerge AS-40 | 4.3 | less than 3 Min. |
| 2. | 8% $H_2O_2$ 0.5M (5.9%) Succinic Acid 0.5% BioTerge AS-40 | 4.2 | 3.5 Min. |
| 3. | 8% $H_2O_2$ 0.25M (2.95%) Succinic Acid 0.5% BioTerge AS-40 | 4.2 | 3.5 Min. |
| 4. | 8% $H_2O_2$ 0.125M (1.47%) Succinic Acid 0.5% BioTerge AS-40 | 4.2 | 3.0 Min. |

As demonstrated in Tables VII and VIII at equal molarities, and equal pH values of about 4.2, there is very little difference between acetic acid and succinic acid to enhance spore kill in combination with 8% $H_2O_2$ and BioTerge AS-40.

As one covers a range from a high of 1.0M to a low of 0.125M, an eight-fold difference, the rate of spore kill changes very little from the slowest rate of about 4.0 min. to the fastest rate of about 3.0 min. The change is consistent with 1.0M acetic or succinic acid always snowing a faster spore kill than lesser concentrations, but it is a very small change.

8% $H_2O_2$ (2.35M) plus 1% (0.17M) acetic acid, or plus 0.2M acetic acid at pH 2.5 (all of the acetic acid in the acid form), or pH—4.3 (about half of the acetic acid in the acid form, and half as sodium acetate) killed spores of *C. sporogenes* and *B. subtilis* within 30 min. at 20°±1° C. More *B. subtilis* spores were killed within 15 min. at the lower pH (about 2.5) than at the higher pH (about 4.3), but complete kill happened within 30 min. for both pH values.

8% $H_2O_2$ plus 0.5% malonic acid or 0.5% succinic acid

| | |
|---|---|
| COOH—$CH_2$—COOH | COOH—$CH_2$—$CH_2$—COOH |
| Malonic Acid | Succinic Acid | all at pH 1.8–2.4 sterilized porcelain cylinders labeled with *C. sporogenes* within 30 min. at 20°±1° C.

8% $H_2O_2$ plus 0.2M glutaric acid (COOH—$CH_2$—$CH_2$—$CH_2$—COOH) was less active than succinic acid, and more active than citric acid. 8% $H_2O_2$ plus 0.2M glutaric acid at pH 2.2–2.6 killed wet *B. subtilis* spores within 60 min. at 20°±1° C., but not within 30 min., and sterilized *C. sporogenes* dried onto porcelain cylinders within 30 min. at 20°±1° C., pH 2.2, but not at pH 5.0 (where half of the glutaric acid exists as the acid and half exists as the sodium salt).

8% $H_2O_2$ plus 0.2M citric acid, a tricarboxylic acid, COOH—$CH_2$—COHCOOH—$CH_2$—COOH, did not kill wet *B. subtilis* spores at all within 60 min. at 20°±1° C. either at pH 2.0 or 6.4. Similarly, 8% $H_2O_2$ plus 0.2M citric acid at pH 1.9 or 6.6 could not sterilize any *C. sporogenes*-labeled cylinders at 20°±1° C.

The above tests lead to the following observations:

The initial testing was performed because of the similar structural chemistry between peracetic acid ($CH_3$—COOOH) and acetic acid ($CH_3$—COOH). The following formulations were tested: (1) 6% $H_2O_2$, pH 4.7, (2) 6% $H_2O_2$+0.5% acetic acid, pH 2.7, (3) 6% $H_2O_2$+0.5% sodium acetate, pH 6.7, (4) 0.5% acetic acid, pH 2.8, and (5) 0.5% sodium acetate, pH 7.7. Unglazed porcelain cylinders labeled with approx. $10^6$ dry spores of *Clostridium sporogenes* according to the methods of the AOAC Sporicidal Test 966.04 were exposed to these above five formulations for 30 min. at 20°±1° C. Of a total of 20 spore-labeled cylinders, 18 were sterilized when exposed to 6% $H_2O_2$+0.5% acetic acid (Formula #2 above). None (zero) of 20 were sterilized when similarly exposed to the other formulas.

Two cylinders from a total of 20 tested were not sterilized by formula #2 above. Next tested were increased concentrations of $H_2O_2$ and acetic acid for ability to sterilize dry cylinders labeled with *C. sporogenes.* 8% $H_2O_2$ plus 2% acetic acid sterilized within 20 min. at 20°±1° C., 8% $H_2O_2$ plus 1% acetic acid, and also 8% $H_2O_2$ plus 0.5% acetic acid sterilized within 30 min. at 20°±1° C.

The above tests were then expanded to determine if other weak di- or poly carboxylic acids could act synergistically with $H_2O_2$ for rapid sporicidal activity. The dicarboxylic acids, malonic (COOH—$CH_2$—COOH), and succinic (COOH—$CH_2$—$CH_2$—COOH) were tested. 8% $H_2O_2$ plus 1% acetic acid, pH 2.5, sterilized within 30 min. at 20°±1° C. 8% $H_2O_2$ plus 1% malonic acid, pH 1.8, sterilized 17 cylinders out of 20 within 30 min. at 20°±1° C., and 8% $H_2O_2$ plus 0.5% succinic acid pH 2.4, sterilized 19 cylinders out of 20 within 30 min. at 20°±1° C. The test was *C. sporogenes* on porcelain cylinders.

$H_2O_2$ plus the weak carboxylic acids produce a formula with acidic pH values of 2–3. However, the carboxylic acids can act as buffers by taking them up to a pH value where half of the molecules are in the acid form ($CH_3$—COOH) and half of the molecules are the conjugate base ($CH_3$—COO—). These higher pH values (pH 4–5) might be more compatible with materials than the lower pH values. 8% $H_2O_2$ plus 0.2M citric acid (a tricarboxylic acid) did not sterilize *C. sporogenes*-labeled cylinders at pH 1.9 or 6.6. 8% $H_2O_2$ plus 0.2M glutaric acid (COOH—$CH_2$—$CH_2$—$CH_2$—COOH) did sterilize within 30 min. at 20°±1° C. at pH 2.2, but not at pH 5.0. 8% $H_2O_2$ plus 0.2M succinic acid (COOH—$CH_2$—$CH_2$—COOH) sterilized within 30 min. at 20°±1° C. at both pH 1.8 and 3.0. 8% $H_2O_2$ plus 0.2M acetic acid sterilized within 30 min. at 20°±1° C. at both pH 2.7 and 4.2. These studies were all against *C. sporogenes*-labeled cylinders.

Studies have been performed using these formulations against *Bacillus subtilis* spores both in the form of dry spores carried on porcelain cylinders, or wet spores in suspension. The results against *B. subtilis* are consistent with results against *C. sporogenes* as follows: 8% $H_2O_2$ plus 0.2M citric acid at pH 2.0 or 6.4 did not kill wet spores of *B. subtilis* within 60 min. at 20°±1° C. 8% $H_2O_2$ plus 0.2M acetic acid (pH 2.7 or pH 4.2) killed wet or dry *B. subtilis* within 30 min. at 20°±1° C. 8% $H_2O_2$+0.2M malonic killed wet spores of *B. subtilis* faster at pH 1.8 than at pH 3.0. 8% $H_2O_2$+0.2M succinic acid at pH 2.4 killed wet or dry spores of *B. subtilis,* but was less effective at pH 4.2. 8% $H_2O_2$ plus 0.2M glutaric acid was more effective against wet spores of *B. subtilis* at pH 2.6 than at pH 5.0. The specific test results are described below.

This example compares the rate of kill of *B. subtilis* spores by formulations of $H_2O_2$ plus acetic, malonic, or succinic acid. The test method utilized wet spores of *B. subtilis* in suspension (not on carriers). This is a quantitative test that allows comparison of formulations with more precision than a qualitative (sterile or not sterile) test such as the AOAC Sporicidal Test. The starting number of cells of *B. subtilis* was very high at about $3.1\times10^8$ cells. It required about 60 min. of exposure time at 20°±1° C. to kill all of these cells.

The results were as follows:

TABLE IX

| Formula Number | Formula Description | pH | D-values in Min. |
|---|---|---|---|
| 1. | 8% $H_2O_2$ + 0.2$\underline{M}$ (1.2%) acetic acid, | pH 2.7 | 7.5 |
| 2. | 8% $H_2O_2$ + 0.2$\underline{M}$ (1.2%) acetic acid, | pH 4.2 | 8.5 |
| 3. | 8% $H_2O_2$ + 0.2$\underline{M}$ (2.1%) malonic acid, | pH 1.8 | 8.5 |
| 4. | 8% $H_2O_2$ + 0.2$\underline{M}$ (2.1%) malonic acid, | pH 3.0 | 7.8 |
| 5. | 8% $H_2O_2$ + 0.2$\underline{M}$ (2.4%) succinic acid, | pH 2.4 | 6.0 |
| 6. | 8% $H_2O_2$ + 0.2$\underline{M}$ (2.4%) succinic acid, | pH 4.2 | 9.0 |

The D-values were calculated as the time to kill four $log_{10}$ of *B. subtilis* divided by four.

The general conclusion is that combinations of 8% $H_2O_2$ plus acetic, malonic, or succinic acid have about the same rate of kill of *B. subtilis* spores (wet) in suspension. The more acid pH values of about 2–3 were consistently killing faster than the less acid pH values of about 4.

Next, three formulations of 8% $H_2O_2$ (a pH 2.00 succinic acid formulation, a pH 4.35 succinic acid formulation, and a pH 4.23 acetic acid formulation) were placed into plastic trays with loose-fitting plastic lids. Various combinations of stainless steel instruments, endoscope parts, and respiratory care equipment were soaked in the formulations for fourteen days at ambient temperature (22°±2° C.). Two marketed disinfectants (2% alkaline glutaraldehyde, and 0.25% quaternary ammonium compounds in 15% isopropanol) were also used in the study for comparison.

After fourteen days of continuous soaking in the $H_2O_2$ formulations, quality Sklarlite® stainless steel instruments appeared unchanged. Less expensive, poorly-plated instruments became mildly tarnished by the three $H_2O_2$ formulations. By comparison, the quality Sklar® instruments had become slightly rusted by 2% alkaline gluteraldehyde and extremely rusted by the alcohol disinfectant. With one exception, the endoscope parts and respiratory care equipment appeared unchanged by any of the $H_2O_2$+carboxylic acid formulations. The details of the test are reported below.

The study of this example was limited to visual observations of materials compatibility with the formulations as previously described. In particular, the formulations used were:

Formulation #1

8% $H_2O_2$ 0.5M Acetic Acid 0.25% Bio-Terge AS-40 detergent 0.25M NaOH Prepared with USP purified deionized $H_2O$ pH 4.23

Formulation #2

8% $H_2O_2$ 0.5M Succinic Acid 0.25% Bio-Terge AS-40 detergent 0.5M NaOH Prepared with USP purified deionized $H_2O$ pH 4.35

Formulation #3

8% $H_2O_2$ 0.5M Succinic Acid 0.25% Bio-Terge AS-40 detergent Prepared with USP purified deionized $H_2O$ pH 2.00

The materials were soaked in the above test formulas or in:

0.25% quaternary ammonium chloride in 15% isopropanol, or

2% alkaline glutaraldehyde.

The items soaked were:

Eight Cambro plastic trays with loose-fitting plastic lids;

Five Sklarlite® stainless steel Halsted Mosq. STR 5" Hemostats. Sklar Hospital Catalog #23-2105. New;

Three pair of inexpensive scissors, poorly plated, but otherwise in good condition with no tarnish;

One set of respiratory care equipment:

- a "Y" plastic connector
- a face mask
- an endotracheal tube
- a section of a blue latex breathing bag Two sets of endoscope parts, the first being: insertion tube, bending rubber, biopsy channel, pliable≈⅓" id connector, hard≈½" id connector, and hard≈½" diam. cap.

The second set was an insertion tube, bending rubber, biopsy channel, hard≈½" id connector, hard≈½" diam. cap, and hard≈½" diam. cap with stainless steel opening.

All parts were new or in good condition at the start.

Two hundred ml of disinfectant and various instruments, parts, and equipment were placed into eight plastic trays. The trays were covered and left at ambient temperature (22°±2° C.) for fourteen days. Observations were made at various intervals throughout the fourteen day time. The results are reported in Table X, below.

Results:

TABLE X

Observations of Materials Compatibility
Exposure Time to Disinfectant

| Disinfectant | Instrument | Day 2 | Day 3 | Day 6 | Day 9 | Day 14 |
|---|---|---|---|---|---|---|
| 2% Alkaline glutaraldehyde | Hemostats | N.C. | N.C. | N.C. | slight rust in hinge | slight rust in hinge |
| 0.25% quaternary ammonium chloride in 15% isopropanol Formulation #1 | Hemostats | N.C. | 2–3 mm rust spot in hinge | major rust in hinge | major rust in hinge | major rust in hinge |
| 8% $H_2O_2$ 0.5M Acetic Acid 0.25% Bio-Terge AS-40 0.25M NaOH pH = 4.23 Formulation #3 | Hemostats | N.C. | N.C. | N.C. | N.C. | N.C. |
| | Scissors | N.C. | N.C. | Mild tarnish | Tarnish on handle & hinges | Tarnish on handle & hinges |
| 8% $H_2O_2$ 0.5M Succinic Acid 0.25% Bio-Terge AS-40 pH = 2.00 Formulation #2 | Hemostats | N.C. | N.C. | N.C. | N.C. | N.C. |
| | Scissors | N.C. | N.C. | Mild tarnish | Tarnish on handle & hinges | Tarnish on handle & hinges |
| 8% $H_2O_2$ 0.5M Succinic Acid 0.25% Bio-Terge AS-40 0.5M NaOH pH = 4.35 Formulation #2 | Hemostats | N.C. | N.C. | N.C. | N.C. | N.C. |
| | Scissors | N.C. | Slight tarnish in hinge | Mild tarnish | Tarnish on handle & hinges | Tarnish on handle & hinges |
| 8% $H_2O_2$ 0.5M Succinic Acid 0.25% Bio-Terge AS-40 0.5M NaOH pH = 4.35 Formulation #3 | "Y" Connector | N.C | N.C. | N.C. | N.C. | N.C. |
| | Face Mask | N.C. | N.C. | N.C. | N.C. | N.C. |
| | Endotracheal Tube | N.C. | N.C. | N.C. | N.C. | N.C. |
| | Breathing Tube | N.C. | N.C. | N.C. | N.C. | N.C. |
| 8% $H_2O_2$ 0.5M Succinic Acid 0.25% Bio-Terge AS-40 pH = 2.00 | Insertion Tube | N.C. | N.C. | N.C. | N.C. | N.C. |
| | Biopsy Channel | N.C. | N.C. | N.C. | N.C. | N.C. |
| | Bending Rubber | N.C. | N.C. | N.C. | N.C. | N.C. |
| | Pliable Connector | N.C. | N.C. | N.C. | N.C. | Broke into small pieces |
| | Hard Connector | N.C. | N.C. | N.C. | N.C. | N.C. |
| | Hard Cap | N.C. | N.C. | N.C. | N.C. | N.C. |

TABLE X-continued

Observations of Materials Compatibility
Exposure Time to Disinfectant

| Disinfectant | Instrument | Day 2 | Day 3 | Day 6 | Day 9 | Day 14 |
|---|---|---|---|---|---|---|
| Formulation #2 | | | | | | |
| 8% H$_2$O$_2$ | Insertion Tube | N.C. | N.C. | N.C. | N.C. | N.C. |
| 0.5M Succinic Acid | Biopsy Channel | N.C. | N.C. | N.C. | N.C. | N.C. |
| 0.25% Bio-Terge AS-40 | Bending Rubber | N.C. | N.C. | N.C. | N.C. | N.C. |
| 0.5M NaOH | Hard Cap | N.C. | N.C | N.C. | N.C. | N.C. |
| pH = 4.35 | Hard Connector | N.C. | N.C. | N.C. | N.C. | N.C. |
| | Hard Cap with stainless steel opening | N.C. | N.C. | N.C. | N.C. | N.C. |

N.C. = No Change

As seen from data in Table X, formulations 1, 2 and 3 did not cause any apparent changes to the quality Sklarlite® instruments. The formulations did cause some tarnishing of the poorly-plated instruments. The pH 2.00 8% H$_2$O$_2$, succinic acid formulation caused more tarnishing than the other two formulations.

In comparison, 2% alkaline gluteraldehyde caused minor rusting of the quality Sklarlite® hemostats, and 0.25% quaternary ammonium chloride in 15% isopropanol caused major rusting of the Sklarlite® hemostats.

The pH 2.00, 8% H$_2$O$_2$, succinic acid formulation did cause major disintegration of one piece, the pliable endoscope connector, which fell apart when squeezed slightly. It was not known whether this aberation was caused by the nature of the elastomer of this single part or not. However, no other parts during testing showed any damage by succinic acid compositions.

Formulations 2 and 3 did not cause any apparent change to the other endoscope parts. Formulation 2 did not cause any apparent change to the respiratory care equipment.

While not wishing to be bound by a theory of why the invention works, the data in the above examples demonstrates an apparent reaction and a synergistic relationship between hydrogen peroxide specifically and certain of the described carboxylic acids. It probably extends to peroxides in general that release hydroxyl free radicals that together cause rapid kill of bacterial spores and all other microbes at ambient (approximately 18° C.–24° C.) temperatures. There is no need for heating, and moreover the kill is generally accomplished within 30 min. It also suggests that a reaction product may be formed in situ which could be isolated and itself used as the quick acting sterilant, and thus the invention contemplates such an embodiment as being within its scope.

It therefore can be seen that the invention accomplishes all of its stated objectives.

What is claimed is:

1. A low odor, aqueous quick acting room temperature disinfecting and/or sterilization solution that is non-corrosive to metals and elastomers used in medical instruments which are in need of sterilization and disinfection having a pH within the range of from about 2.0 to about 6.0 consisting essentially of:
   from about 1% to about 30% by weight of a peroxide; and
   from about 1% to about 30% by weight of malonic acid, or salt form there of, said solution being effective at room temperature to disinfect medical instruments within 30 minutes without corroding surfaces of said medical instruments.

2. An aqueous disinfecting and/or sterilizing solution of claim 1 wherein the peroxide has a concentration of from about 1.0% by weight to about 12% by weight.

3. An aqueous disinfecting and/or sterilizing solution of claim 2 wherein the peroxide concentration is from about 6% by weight to about 10% by weight.

4. An aqueous disinfecting and/or sterilization solution of claim 1 wherein the peroxide capable of releasing hydroxyl free radicals is selected from the group consisting of hydrogen peroxide, alkyl peroxides, aryl peroxides, and alkylidine peroxides.

5. An aqueous disinfecting and/or sterilization solution of claim 1 wherein the concentration of malonic acid or salt form thereof is from about 1% by weight to about 12% by weight.

6. An aqueous disinfecting and/or sterilization solution of claim 1 wherein the concentration of malonic acid or salt form thereof is from about 3% by weight to about 6% by weight.

7. An aqueous disinfectant and/or sterilization solution of claim 2 which includes minors selected from the group consisting of compatible corrosion inhibitors, buffers, diluents, odorants and dyes.

8. A low odor aqueous quick acting, relatively non-toxic room temperature disinfecting and/or sterilization solution that is non-corrosive to metals and elastomers used in medical instruments having a pH within the range of from about 2.0 to about 6.0, consisting essentially of:
   from about 1.0% to about 30% by weight of a peroxide capable of releasing hydroxyl free radicals;
   from about 1.0% to about 30% by weight of malonic acid, or salt form thereof, said solution being effective at room temperature to disinfect medical instruments within 30 minutes without corroding surfaces of said medical instruments; and
   from about 0.1% to about 1.0% by weight of a peroxide and organic acid compatible anionic or nonionic surfactant.

9. An aqueous disinfecting and/or sterilization solution of claim 8 wherein the concentration of surfactant is from about 0.1% by weight to about 0.5% by weight.

10. An aqueous disinfecting and/or sterilization solution of claim 8 wherein the surfactant is a nonionic detergent.

11. An aqueous disinfectant and/or sterilant of claim 10 wherein the nonionic detergent is an ether linked surfactant.

12. A process of quick action room temperature disinfecting of medical instruments without damaging the instruments, consisting essentially of:
   contacting at room temperature the instruments for a sterilizing effective amount of time with an odor-free aqueous disinfecting solution that is non-corrosive having a pH within the range of from about 2.0 to about 6.0 which consists essentially of from about 1.0% by weight to about 30.0% by weight of hydrogen peroxide and from about 1.0% by weight to about 30.0% by weight of malonic acid, or salt form thereof, said solution being effective at room temperature to disinfect medical instruments within 30 minutes without corroding surfaces of said medical instruments.

13. A process of quick action room temperature disinfecting of medical instruments without damaging the instruments, consisting essentially of:

contacting at room temperature the instruments for a sterilizing effective amount of time with an odor-free aqueous disinfecting solution that is non-corrosive having a pH within the range of from about 2.0 to about 6.0 which consists essentially of from about 1.0% by weight to about 30.0% by weight of hydrogen peroxide, from about 1.0% by weight to 30.0% by weight of malonic acid, or salt form thereof, and from about 0.1% by weight to 1% by weight of a peroxide and organic acid compatible surfactant, said solution being effective at room temperature to disinfect medical instruments within 30 minutes without corroding surfaces of said medical instruments.

14. The process of claim 13 wherein the surfactant is selected from the group consisting of anionic and nonionic detergents.

15. The process of claim 14 wherein the detergent is a nonionic surfactant.

16. The process of claim 15 wherein the detergent is an ether linked surfactant.

* * * * *